(12) United States Patent
Drahos

(10) Patent No.: US 7,407,793 B2
(45) Date of Patent: Aug. 5, 2008

(54) CONSORTIUM OF NITRIFYING BACTERIA

(75) Inventor: David J. Drahos, Roanoke, VA (US)

(73) Assignee: Novozymes Biologicals, Inc., Salem, VA (US)

( * ) Notice: Subject to any disclaimer, the term of this patent is extended or adjusted under 35 U.S.C. 154(b) by 0 days.

(21) Appl. No.: 11/248,383

(22) Filed: Oct. 11, 2005

(65) Prior Publication Data

US 2006/0081532 A1 Apr. 20, 2006

Related U.S. Application Data

(60) Provisional application No. 60/618,920, filed on Oct. 14, 2004.

(51) Int. Cl.
- C12N 1/12 (2006.01)
- C12N 1/00 (2006.01)
- C02F 3/00 (2006.01)
- C02F 3/34 (2006.01)

(52) U.S. Cl. .................. 435/252.4; 435/243; 435/252.1; 210/601; 210/606

(58) Field of Classification Search ................. 435/243, 435/252.1, 252.4; 210/601, 606
See application file for complete search history.

(56) References Cited

U.S. PATENT DOCUMENTS

| 6,207,440 | B1 | 3/2001 | Hovanec | |
|---|---|---|---|---|
| 2004/0101944 | A1* | 5/2004 | Willuweit et al. | ........... 435/243 |

FOREIGN PATENT DOCUMENTS

| WO | WO 02/24583 | * | 3/2002 |
|---|---|---|---|

OTHER PUBLICATIONS

Suwa et al., 1997, Journal of General Applied Microbiology, 43, 373-379.*
Koops et al., Genus I. *Nitrosomonas winogradskyi*, in Bergey's Manual of Systematic Bacteriology, vol. Two, The Proteobacteria Part C, The Alpha-, Beta-, Delta-, and Epsilonproteobacteria, 2005, Springer US, Second Ed., 864-867.*
Spieck et al., Genus VI. *Nitrobacter winogradskyi*, in Bergey's Manual of Systematic Bacteriology, vol. Two, The Proteobacteria Part C, The Alpha-, Beta-, Delta-, and Epsilonproteobacteria, 2005, Springer US, Second Ed., 461-468.*
Chain et al., Journal of Bacteriology, vol. 185, No. 9, pp. 2759-2773 (2003).
Fouratt et al., Fems Microbiology Ecology, vol. 43, pp. 277-286 (2003).
Database GenCore on STN, AN AB00702, Suwa et al. Jan. 24, 1997. "Phylogenetic relationships of activated sludge isolates of ammonia oxidizers with different sensitivities to ammonium sulfate".
Technical Data Sheet for Nitrobac® 20L sold by InterBio (2000).
Technical Data Sheet for Nitrotox™ sold by InterBio (2000).

* cited by examiner

*Primary Examiner*—Ruth A Davis
*Assistant Examiner*—Sheridan R MacAuley
(74) *Attorney, Agent, or Firm*—Elias Lambiris

(57) ABSTRACT

The present invention relates to a consortium of *Nitrosomonas eutropha* and *Nitrobacter winogradskyi*, which is more effective at removing ammonia and nitrite than the commonly used consortium of *Nitrosomonas europea* and *Nitrobacter winogradskyi*, particularly in aquaculture such as shrimp ponds. Supplementation of the consortium in aquaculture such as shrimp ponds may lead to an increase in total yield, an increase in size, a decrease in Food Conversion Ratio (less food required per kg of shrimp obtained), and an increase in total per pond sales.

2 Claims, No Drawings

ID NO: 1 and 2, respectively. Based on
CONSORTIUM OF NITRIFYING BACTERIA

CROSS-REFERENCE TO RELATED APPLICATIONS

This application claims priority or the benefit under 35 U.S.C. 119 of U.S. provisional application No. 60/618,920 filed Oct. 14, 2004, the contents of which are fully incorporated herein by reference.

REFERENCE TO A SEQUENCE LISTING

This application contains a sequence listing, which is incorporated herein by reference.

BACKGROUND OF THE INVENTION

1. Field of the Invention

The present invention relates to a consortium of nitrifying bacteria and to its use, particularly in aquaculture.

2. Description of Related Art

In aquaculture systems, the accumulation of high concentrations of ammonia and nitrite, toxic to aquatic organisms, is commonly prevented by active removal by nitrifying microorganisms including ammonia oxidizing bacteria (AOB) and nitrite oxidizing bacteria (NOB). Traditionally, the bacteria responsible for the oxidation of ammonia and nitrite in aquaria were considered to be *Nitrosomonas europaea* and *Nitrobacter winogradskyi*. In newly set-up aquaria, ammonia and nitrite can reach concentrations toxic to fish, crustaceans, and other aquatic invertebrates before a sufficient biomass of AOB and NOB become established. To reduce the length of time for establishment of NOB, commercial preparations of these organisms, are available to seed the aquarium environment, including mixed cultures of autotrophic AOB and NOB organisms.

U.S. Patent Publication No. 2004/0101944 relates to a microbiological culture and use of this culture, inter alia, for removing harmful substances, such as nitrogen compounds; the microorganisms may be selected from nitrification microorganisms, e.g., *Nitrosomonas eutropha* or *Nitrobacter winogradskyi*.

U.S. Pat. No. 6,207,440 describes an isolated bacterial strain capable of oxidizing nitrite to nitrate and a method of use thereof for preventing or alleviating the accumulation of nitrite in an aqueous medium.

It is an object of the present invention to provide an improved consortium of nitrifying bacteria.

SUMMARY OF THE INVENTION

The inventors have found that a consortium of *Nitrosomonas eutropha* and *Nitrobacter winogradskyi* is more effective at removing ammonia than the commonly used consortium of *Nitrosomonas europaea* and *Nitrobacter winogradskyi*, particularly in aquaculture, e.g., with growing shrimp. Supplementation of the consortium in aquaculture such as shrimp ponds may lead to an increase in total yield, an increase in size, a decrease in Food Conversion Ratio (less food required per kg of shrimp obtained), and an increase in total per pond sales.

Accordingly, the invention provides such a consortium of nitrifying bacteria and its use in aquaculture, particularly in shrimp ponds.

DETAILED DESCRIPTION OF THE INVENTION

Microbial Deposit

A representative bacterial consortium was isolated from a sample from natural sources collected before 1994. It was deposited for patent purposes under the terms of the Budapest Treaty at the ATCC (American Type Culture Collection), 10801 University Blvd., Manassas, Va. 20108 USA. The deposit was made on Sep. 23, 2004 and was accorded deposit number PTA-6232 by Novozymes Biologicals Inc.

The deposited consortium contains an ammonia oxidizing bacterium and a nitrite oxidizing bacterium. For taxonomic purposes, the 16S rDNA of the two organisms was sequenced and is given as SEQ ID NO: 1 and 2, respectively. Based on the sequence with all other published sequences publicly available through GenBank (*Nucleic Acids Research* 2004 Jan. 1; 32(1):23-6), the ammonia oxidizing bacterium was classified as *Nitrosomonas eutropha* (Koops et al., *J. Gen. Microbiol.* 1991, 137, 1689-1699), and the nitrite oxidizing bacterium was classified as *Nitrobacter winogradskyi*.

Nitrifying Consortium

The nitrifying consortium comprises an ammonia oxidizing bacterium (AOB) and a nitrite oxidizing bacterium (NOB).

The AOB may belong to the species *Nitrosomonas eutropha* and/or it may have a 16S rDNA sequence which is less than 2% dissimilar from (more than 98% identical to) SEQ ID NO: 1, particularly less than 1% dissimilar (more than 99% identical). Preferably, the AOB has a 16S rDNA sequence which is SEQ ID NO: 1 or is the *Nitrosomonas eutropha* strain contained in ATCC PTA-6232.

The NOB may belong to *Nitrobacter winogradskyi* and/or it may have a 16S rDNA sequence which is less than 10% dissimilar from (more than 90% identical to) SEQ ID NO: 2, particularly less than 6% or less than 3% dissimilar (more than 94% or more than 97% identical). Preferably, the NOB has a 16S rDNA sequence which is SEQ ID NO: 2 or is the *Nitrobacter winogradskyi* strain contained in ATCC PTA-6232.

A given sequence may be aligned with SEQ ID NO: 1 or 2 and the dissimilarity or identity may be calculated using the BLAST program (Basic Local Alignment Search Tool, available at www.ebi.ac.uk/blast/index.html where the expectation value is set at 10, the penalty for nucleotide mismatch is −3, the reward for match is +1, the gap opening penalty is −5 and the gap extension penalty is −2. A sequence alignment may be produced using the CLUSTALW program from the PHYLIP Phylogenetic Inference Package (Felsenstein, J. 1989. PHYLIP—Phylogeny Inference Package (Version 3.2). Cladistics 5: 164-166). The Accurate Method using the IUB/BESTFIT weight matrix may be used with a gap penalty of −15 and an extension penalty of −6.66. The resulting alignment may be used to determine % dissimilarity (and % identity) using the DNADIST program from PHYLIP according to the Jukes-Cantor model.

The AOB and NOB may be used together with other bacteria, e.g., *Bacillus* such as the commercial product Prawn Bac PB-628 (product of Novozymes Biologicals), *Enterobacter* or *Pseudomonas*.

The nitrifying consortium may be formulated as a liquid, a lyophilized powder, or a biofilm, e.g., on bran or corn gluten. The ammonia oxidizing bacterium will typically be inoculated to an ammonia oxidation rate of about 50-5000 mg $NH_3$—N/L/hr (typically around 800), and the nitrite oxidizing bacterium will typically be inoculated to a nitrite oxidizing rate of about 10-2000 mg $NO_2$—N/L/hr (typically around 275).

Ammonia and Nitrite Oxidation Rates

The ammonia oxidation rate is determined by incubating with $NH_4Cl$ as substrate at 30° C. and pH 8.0. The nitrite oxidation rate is determined by incubating with $NaNO_2$ as substrate at 30° C. and pH 7.5-7.8.

Cultivation

The consortium may be cultivated in a batch culture by methods known in the art. See, e.g., H Koops, U Purkhold, A Pommerening-Roser, G Timmermann, and M Wagner, "The Lithoautotrophic Amnmonia-Oxidizing Bacteria," in M. Dworkin et al., eds., The Prokaryotes: An Evolving Electronic Resource for the Microbiological Community, 3rd edition, release 3.13, 2004, Springer-Verlag, New York.

The nitrifying consortium may be formulated as a liquid, a lyophilized powder, or a biofilm, e.g., on bran or corn gluten. It will typically be formulated to an ammonia oxidation rate of about 50-5000 mg $NH_3$—N/L/hr (e.g., around 800), and a nitrite oxidizing rate of about 10-2000 mg $NO_2$—N/L/hr (e.g., around 275).

Use of Consortium

The consortium may be used for nitrifying an ammonia-containing or nitrite-containing liquid. Thus, It may be used for raising aquatic organisms such as fish (fresh or saltwater fish) or crustaceans (e.g., shrimp), particularly for the production of foodstocks in aquaculture, to keep the levels of ammonia and nitrite in the aquaculture container below harmful concentrations. The aquatic organisms may be raised in liquid (fresh or salt water) in a container such as an aquaculture container, a tank, an aquarium, a pond, an outdoor commercial or ornamental fish or shrimp pond, or a grow-out pond. Thus, supplementation of the microorganisms to shrimp ponds used in marine shrimp production by intensive farming may serve to reduce hazardous organic and inorganic wastes to environmentally safe levels.

Typically, the nitrifying consortium concentrate is added to the aquaculture container at the rate of 0.5-300 liters per 500,000 liters treated, e.g., 1-300 liters per 500,000 liters treated, with a preferred treatment regime of about 2 liters of nitrifying consortium per 500,000 liters water per week over the course of at 10 week treatment period. The ammonia oxidizing bacterium is typically inoculated to a $NH_3$ oxidation rate of 0.01-10 mg $NH_3$—N/L/hr, e.g., 0.03-3 or 0.1-10 mg $NH_3$—N/L/hr, particularly 0.3-3 mg $NH_3$—N/L/hr, and the nitrite oxidizing bacterium is typically inoculated to a $NO_2$ oxidation rate of 0.003-3 mg $NO_2$—N/L/hr, e.g., 0.03-3 mg $NO_2$—N/L/hr, particularly 0.01-1 or 0.1-1 mg $NO_2$—N/L/hr.

The liquid in the pond or aquarium may vary in salinity from 0-36 ppt (parts per thousand), with a preferred salinity range of 4-22 ppt. The temperature may be about 18-38° C., typically around 30° C. The pH may be about 6.8-8.5. The aquaculture container may be aerated by conventional means such as paddle wheels or jet pumps, typically to 40-100% oxygen saturation, or a dissolved oxygen of 3.5-7.5 mg/L. The aquaculture container may also be unaerated by non-mechanical, natural means.

An antibiotic such as cycloheximide may be added to inhibit the growth of protists such as amoebas.

Other environmental settings where ammonia and/or nitrite has reached detrimental levels, such as in various industrial wastewater treatment facilities, municipal waste treatment, or ornamental ponds may benefit by the addition of similar amounts of nitrifying consortium on a regular basis, depending on hydraulic retention time and initial ammonia and nitrite levels.

EXAMPLES

Example 1

Ammonia Oxidation in Flasks

For the flask study, the starting substrate solution was water taken from active shrimp aquarium tanks where shrimp had been actively growing for 4 days, producing their normal ammonia waste under carefully maintained conditions of temperature, in 4 ppt salt-water media buffered to pH 8, aerated to a target DO (dissolved oxygen; 4-5 mg/L $O_2$) level, incubated at 30° C., and provided specific levels of standard food pellets (5-10% of total shrimp weight per tank per day). After 4 days, ammonia had accumulated to approximately 1.4-2.0 ppm $NH_3$, which was a level beginning to be harmful to further shrimp growth. This media was filtered to remove background microbes (heterotrophs) and split into shake flasks for the treatment study. The flasks were inoculated with the following strains to the indicated oxidation rates:

|  | Ammonia ($NH_3$) oxidizing bacterium | Nitrite ($NO_2$) oxidizing bacterium | $NH_3$ oxidation rate (mg $NH_3$-N/L/hr) | $NO_2$ oxidation rate (mg $NO_2$-N/L/hr) |
|---|---|---|---|---|
| Control | None | None | 0 | 0 |
| Prior art | Nitrosomonas europea | Nitrobacter winogradskyi | 1.0 | 0.3 |
| Reference | Nitrosomonas eutropha | None | 1.0 | 0 |
| Invention | Nitrosomonas eutropha | Nitrobacter winogradskyi | 1.0 | 0.3 |

The following three key elements were measured from day 0 to day 8 in the nitrification process Ammonia ($NH_4^+$), Nitrite ($NO_2$) and nitrate ($NO_3$).

| Days | Control | Prior art | Reference | Invention |
|---|---|---|---|---|
| 1. Ammonium (ppm $NH_4^+$) change: | | | | |
| 0 | 9 | 9 | 9 | 9 |
| 1 | 9.0 | 6.2 | 4.9 | 4.1 |
| 2 | 8.9 | 4.3 | 0.6 | 0.6 |
| 3 | 8.7 | 3.4 | 0.6 | 0.6 |
| 6 | 8.7 | 0.6 | 0.4 | 0.3 |
| 7 | 8.4 | 0.3 | 0.4 | 0 |
| 8 | 8.2 | 0.2 | 0.3 | 0 |
| 2. Nitrite (ppm $NO_2$) change | | | | |
| 0 | 0 | 0 | 0 | 0 |
| 1 | 0 | 1.7 | 0 | 1.1 |
| 2 | 0 | 0 | 21.1 | 0 |
| 3 | 0 | 0 | 22.0 | 0 |
| 6 | 0 | 0 | 21.9 | 0 |
| 7 | 0 | 0 | 21.8 | 0 |
| 8 | 0 | 0 | 21.1 | 0 |
| 3. Nitrate (ppm $NO_3$) change | | | | |
| 0 | 0 | 0 | 0 | 0 |
| 1 | 0 | 4.4 | 0 | 4.8 |
| 2 | 0 | 10.5 | 0 | 12.3 |
| 3 | 0 | 12.5 | 0 | 13.7 |
| 6 | 0 | 18.7 | 0 | 19.4 |

-continued

| Days | Control | Prior art | Reference | Invention |
|---|---|---|---|---|
| 7 | 0 | 19.4 | 0 | 19.9 |
| 8 | 0 | 19.5 | 0 | 20.4 |

The results show clearly that the consortium of *Nitrosomonas eutropha* and *Nitrobacter winogradskyi* was the most effective at oxidizing ammonia to nitrate. The reference with only the ammonia oxidizing bacterium *Nitrosomonas eutropha* could oxidize ammonia to nitrite, but could not oxidize the nitrite to nitrate. The prior-art consortium could oxidize ammonia to nitrate, but was less effective at removing ammonia.

Example 2

Ammonia Oxidation in Shrimp Tanks

For the Shrimp Tank Study, shrimp were grown in the aquarium tanks as described in Example 1, and inoculated only once on the first day of the study. The inoculation rates used in the tank study were $1/10^{th}$ the rates described in Example 1. Typically, 2.5 ml of a nitrification strain concentrate with an ammonia oxidation rate of 800 mg $NH_3$—N/L/hr and a nitrite oxidation rate (where applicable) of at least 270 mg $NO_2$—N/L/hr was added to 5 gallons of aquarium salt water. This provided a final ammonia oxidation rate of 0.1 mg $NH_3$—N/L/hr and a nitrite oxidation rate (where applicable) of at least 0.03 mg $NO_2$—N/L/hr. The accumulation of ammonia, nitrite, and nitrate were followed in tanks treated with the same strains as in Example 1. The water also contained heterotrophic bacteria, naturally present from the feed and the shrimp themselves (as in the farm ponds), which may adhere to the flocculated nitrifier consortium and inhibit effective ammonia or nitrite utilization.

| Days | Control | Prior art | Reference | Invention |
|---|---|---|---|---|
| 1. Ammonia (ppm $NH_4^+$) change: | | | | |
| 0 | 0 | 0 | 0 | 0 |
| 1 | 0.9 | 0.8 | 0.7 | 0.9 |
| 2 | 1.6 | 1.5 | 1.5 | 1.3 |
| 3 | 1.8 | 1.6 | 1.4 | 1.2 |
| 6 | 2.1 | 2.2 | 1.1 | 0.7 |
| 7 | 2.3 | 2 | 0.6 | 0.1 |
| 8 | 2.6 | 2.5 | 0.6 | 0.0 |
| 2. Nitrite ($NO_2$) change: | | | | |
| 0 | 0 | 0 | 0 | 0 |
| 1 | 0.03 | 0.01 | 0.06 | 0.037 |
| 2 | 0.06 | 0.06 | 0.29 | 0.35 |
| 3 | 0.06 | 0.07 | 1.74 | 1.32 |
| 6 | 0.06 | 0.07 | 7.04 | 5.12 |
| 7 | 0.06 | 0.06 | 13.92 | 10.24 |
| 8 | 0.04 | 0.04 | 19.20 | 13.80 |
| 3. Nitrate ($NO_3$) change: | | | | |
| 0 | 0 | 0 | 0 | 0 |
| 1 | 0.2 | 0.2 | 0.3 | 0.2 |
| 2 | 0.3 | 0.4 | 0.8 | 0.6 |
| 3 | 0.8 | 0.7 | 1.2 | 3 |
| 6 | 0.4 | 0.5 | 1.3 | 9.2 |
| 7 | 0.4 | 0.5 | 2.2 | 24 |
| 8 | 0.3 | 0.4 | 2.5 | 33 |

Unexpectedly, the consortium of *Nitrosomonas eutropha* and *Nitrobacter winogradskyi* was capable of effective ammonia oxidation even in this natural environment, while the prior-art consortium of *Nitrosomonas europea* and *Nitrobacter winogradskyi* was much less effective. The prior-art consortium was much less effective than the consortium of the invention even though they were nearly equally effective in the flasks against ammonia in Example 1. Note that the level of nitrite ($NO_2$) in the invention is higher than in the reference (due to the superior ammonia-oxidizing activity of the former), and that the level of nitrate ($NO_3^-$) is also higher in the invention as the nitrite formed is converted to nitrate by the nitrite-oxidizing activity of the invention.

Example 3

Field Trial

A field trial was conducted using pre-selected *Litopenaeus vannamei* post-larval (PL) shrimp, obtained from a commercial hatchery, stocked at a density of 110 larvae per $m^2$. Two separate ponds (0.8 hectares each) were treated with a standard regime of the nitrifying microbial product, where 4 gallons of the concentrated Nitrifying consortium were added to each pond at Week 4 post-stocking, followed by 2 gal at Weeks 5 and 6, then 1 gal through Week 13. Over the course of the study, the total amount of AOB bacteria inoculated provided the equivalent of 0.01 mg $NH_3$—N/L/hr and the total amount of NOB bacteria inoculated provided the equivalent of 0.003 mg $NO_2$—N/L/hr. Five additional identically sized and stocked ponds served as the non-treated controls, receiving the same amount of food as the treated ponds All ponds were mechanically aerated to achieve at least 4.5 mg/L $O_2$ during the day.

Water temperature and salinity in the ponds followed typical seasonal fluctuation, with an average temperature range of 27-32° C., and a salinity of 22-24 ppt. Ponds were fed daily, with up to four feedings per day near harvest.

Four of the five non-treated control ponds had succumbed to ammonia stress and viral disease by Week 6. The remaining control pond was cultured to harvest at Day 82, when ammonia levels had caused feeding stress and disease susceptibility. Both of the treated ponds were healthy beyond Day 100.

Shrimp Yield (kg/ha); Feed Conversion Ratio (FCR); and Individual Shrimp Weight (wt/pcs) for the treated ponds were all significantly better than the non-treated control pond for all of these key parameters.

Ammonia nitrogen ($NH_3$—N) and Nitrite nitrogen ($NO_2$—N) were the most important physical parameters followed in this trial. During the first 8 weeks ammonia levels and nitrite levels in all treated ponds remained very low compared to the steady increase observed in measurements taken in all of the control ponds. Apparently, these $NH_3$ and $NO_2$ increases were serious enough to force the early termination of shrimp growth in four of the control ponds due to death. As the grow-out continued, significant increases continued to be observed in the surviving control pond, with very low to near zero levels observed in the treated ponds.

Shrimp retrieved at Week 8 from one of the treated ponds appeared slightly larger than shrimp from a Control Pond and much more active Dumping). This may have been due to the higher ammonia and nitrite levels in the control pond, compared with the relatively low levels in the treated Pond. The final yield from the treated ponds averaged 19.5 kg/ha compared with 5.2 kg/ha from the surviving control pond.

The data indicated a strong, reproducible response from the probiotic treatments, particularly in regards to ammonia and nitrite water quality, and increase in shrimp growth and yield parameters. In addition, a reduction in residual sludge on the shrimp pond basins was reported as dramatically evident in the treated ponds compared with the non-treated control and historical observations of these pond bottoms at harvest.

The invention claimed is:

1. An isolated composition deposited as ATCC PTA-6232, which comprises a *Nitrosomonas eutropha* strain as an ammonia oxidizing strain and a *Nitrobacter* strain as a nitrite oxidizing strain.

2. A process for nitrifying an ammonia-containing or nitrite-containing liquid, comprising growing the bacterial composition of claim 1 in the liquid.

* * * * *

SEQUENCE LISTING

<160> NUMBER OF SEQ ID NOS: 2

<210> SEQ ID NO 1
<211> LENGTH: 1508
<212> TYPE: DNA
<213> ORGANISM: Nitrosomonas eutropha

<400> SEQUENCE: 1

```
tggagagttt gatcctggct cagattgaac gctggcggca tgctttacac atgcaagtcg      60
aacggcagcg ggggcttcgg cctgccggcg agtggcgaac gggtgagtaa tacatcggaa     120
cgtgtccttg agtggggaat aacgcatcga agatgtgct aataccgcat atttctcagg      180
aagaaagcag gggatcgaaa gaccttgcgc taaaggagcg gccgatgtct gattagctag     240
ttggtgaggt aaaggcttac caaggcaacg atcagtagct ggtctgagag gacgatcagc     300
cacactggga ctgagacacg gcccagactc ctacggagg cagcagtggg gaattttgga      360
caatgggcga aagcctgatc cagccatgcc gcgtgagtga agaaggcctt cgggttgtaa     420
agctctttta gtcggaaaga agaattatg gttaatagcc atgatttatg acggtaccga      480
cagaaaaagc accggctaac tacgtgccag cagccgcggt aatacgtagg gtgcgagcgt     540
taatcggaat tactgggcgt aaagggtgcg caggcggcct tgcaagtcag atgtgaaagc     600
cccgggctta acctgggaat tgcgtttgaa actacaaagc tagagtgcag cagaggggag     660
tggaattcca tgtgtagcag tgaaatgcgt agagatgtgg aagaacaccg atggcgaagg     720
cagctccctg ggttgacact gacgctcatg cacgaaagcg tggggagcaa acaggattag     780
ataccctggt agtccacgcc ctaaactatg tcaactagtt gtcggatcta attaaggatt     840
tggtaacgta gctaacgcgt gaagttgacc gcctgggga g tacggtcgca agattaaaac      900
tcaaaggaat tgacggggac ccgcacaagc ggtggattat gtggattaat tcgatgcaac     960
gcgaaaaacc ttacctaccc ttgacatgct tggaatctaa tggagacata agagtgcccg    1020
aaagggagcc aagacacagg tgctgcatgg ctgtcgtcag ctcgtgtcgt gagatgttgg    1080
gttaagtccc gcaacgagcg caaccttgt cactaattgc tatcatttaa aatgagcact     1140
ttagtgagac tgccggtgac aaaccggagg aaggtgggga tgacgtcaag tcctcatggc    1200
ccttatgggt agggcttcac acgtaataca atggcgtgta cagagggttg ccaacccgcg    1260
aggggagcc aatctcagaa agcacgtcgt agtccggatc ggagtctgca actcggctcc     1320
gtgaagtcgg aatcgctagt aatcgcggat cagcatgccg cggtgaatac gttcccgggt    1380
cttgtacaca ccgcccgtca caccatggga gtgattttca ccagaagcag gtagtttaac    1440
cgcaaggagg cgcttgcca cggtgggggt catgactggg gtgaagtcgt aacaaggtag    1500
ccgtagca                                                             1508
```

<210> SEQ ID NO 2
<211> LENGTH: 1464
<212> TYPE: DNA
<213> ORGANISM: Nitrobacter winogradskyi

<400> SEQUENCE: 2

```
agtgattaga gtttgatcat ggctcagagc gaacgctggc ggcaggctta acacatgcaa      60
gtcgaacggg cgtagcaata cgtcagtggc agacgggtga gtaacgcgtg gaacgtacc     120
ttttggttcg gaacaaccca gggaaacttg gctaataccg gataagccc ttacggggaa      180
agatttatcg ccgaaagatc ggcccgcgtc tgattagctt gttggtgagg taacggctca     240
```

```
ccaaggcgac gatcagtagc tggtctgaga ggatgatcag ccacattggg actgagacac    300
ggcccaaact cctacgggag gcagcagtgg ggaatattgg acaatgggcg caagcctgat    360
ccagccatgc cgcgtgagtg atgaaggccc tagggttgta aagctctttt gtgcgggaag    420
ataatgacgg taccgcaaga ataagccccg gctaacttcg tgccagcagc cgcggtaat     480 acgaaggggg ctagcgttgc tcggaattac tgggcgtaaa gggtgcgtag gcgggtcttt    540
aagtcagggg tgaaatcctg gagctcaact ccagaactgc ctttgatact gaggatcttg    600
agttcgggag aggtgagtgg aactgcgagt gtagaggtga aattcgtaga tattcgcaag    660
aacaccagtg gcgaaggcgg ctcactggcc cgatactgac gctgaggcac gaaagcgtgg    720
ggagcaaaca ggattagata ccctggtagt ccacgccgta aacgatgaat gccagcccgt    780
tagtgggttt actcactagt ggcgcagcta acgctttaag cattccgcct ggggagtacg    840
gtcgcaagat taaaactcaa aggaattgac ggggccccgc acaagcggtg gagcatgtgg    900
tttaattcga cgcaacgcgc agaaccttac cagcccttga catgtccatg accggtcgca    960
gagatgtgac cctctcttcg gagcatggag cacaggtgct gcatggctgt cgtcagctcg   1020
tgtcgtgaga tgttgggtta agtcccgcaa cgagcgcaac ccccgtcctt agttgctacc   1080
atttagttga gcactctaag gagactgccg gtgataagcc gcgaggaagg tggggatgac   1140
gtcaagtcct catggccctt acgggctggg ctacacacgt gctacaatgg cggtgacaat   1200
gggaagcaaa ggggtgaccc ctagcaaatc tcaaaaaacc gtctcagttc ggattgggct   1260
ctgcaacccg agcccatgaa gttggaatcg ctagtaatcg tggatcagca tgccacggtg   1320
aatacgttcc cgggccttgt acacaccgcc cgtcacacca tgggagttgg ttttacctga   1380
aggcggtgcg ctaacccgca agggaggcag ccgaccacgg tagggtcagc gactggggtg   1440
aagtcgtaac aaggtaaccg taaa                                          1464
```